United States Patent [19]

Tsuchiya et al.

[11] 4,219,669

[45] Aug. 26, 1980

[54] METHOD OF TREATING MOTHER LIQUOR OF REACTION IN TEREPHTHALIC ACID PRODUCTION

[75] Inventors: Fujio Tsuchiya; Kenzo Yamamoto; Katsunobu Yamaguchi; Akio Okagami, all of Yokohama, Japan

[73] Assignees: JGC Corporation, Tokyo; Orient Kagaku Kogyo K.K., Osaka, both of Japan

[21] Appl. No.: 46,823

[22] Filed: Jun. 8, 1979

[51] Int. Cl.$^2$ .............................................. C07C 51/42
[52] U.S. Cl. .................................................. 562/486
[58] Field of Search ................................ 562/485, 486

Primary Examiner—Alan Siegel
Attorney, Agent, or Firm—Armstrong, Nikaido, Marmelstein & Kubovcik

[57] ABSTRACT

Reaction mother liquor of terephthalic acid production is treated to separate volatile component mainly composed of acetic acid and solid components composed of used catalyst or heavy metal salt(s), residual terephthalic acid and reaction by-products by using combination of a tubular type heater having at least one heating tube of a relatively small diameter and a separation chamber in which the heating tube(s) open(s) at one end thereof.

5 Claims, No Drawings

METHOD OF TREATING MOTHER LIQUOR OF REACTION IN TEREPHTHALIC ACID PRODUCTION

BACKGROUND OF THE INVENTION

1. Field of the Invention

The present invention concerns a method of treating mother liquor of reaction in terephthalic acid production through a liquid phase oxidation of paraxylene.

2. State of the Art

Industrial production of terephthalic acid generally employs a process of oxidizing paraxylene, the raw material, in the presence of a salt or salts of heavy metal(s) such as Co or Co+Mn as a catalyst, with molecular oxygen, in liquid medium of lower aliphatic acid, usually acetic acid. The formed terephthalic acid precipitates in reaction solution and is recovered from the solution by means of separation such as filtration or centrifuge. The mother liquor thus given contains, in addition to the acetic acid medium, catalyst, terephthalic acid which is dissolved or suspended therein, and reaction by-products such as water, paratolyl acid, 4-carboxy benzaldehyde, isophthalic acid, benzoic acid and high polymers.

Heretofore, the mother liquor has been treated by, firstly evaporation procedure to recover major portion of the solvent, acetic acid, and then, by evaporating the concentrated slurry in a thin-film evaporator to recover the rest of the solvent. The thick slurry obtained solidifies after cooling, and heavy metal components in the solid are extracted to regenerate and reuse as the catalyst.

In general, operation of a thin-film evaporator is delicate and troublesome; particularly in treatment of the above described terephthalic acid production process, it is difficult to continue smooth operation, probally due to some contents of the matter to be treated. Consequently, operation of the process, including the oxidation step, has been often interrupted. Moreover, the thick slurry from the thin-film evaporator solidifies through cooling to form a solid mass, which necessitates crushing and atomizing of the mass for the extraction of the heavy metal components.

As solutions for these problems, there has been proposed, to date, addition of an aliphatic ketone to the mother liquor (Japanese Patent Disclosure No. 136634/1976), concentration of the mother liquor to some extent and then addition of aromatic hydrocarbon under heating to distill out acetic acid and to obtain solid components (Japanese Patent Disclosure No. 136635/1976). According to these improved methods, it is possible to realize more efficient solid-liquid separation and to get a solid which can be treated easily. However, introduction of the substances of no direct necessity for the reaction into the process brings about new problem of necessary separation step for the substances.

SUMMARY OF THE INVENTION

It is the object of the present invention to provide a solution of the above mentioned problems in the terephthalic acid production, which does not employ a thin-film evaporator and avoids involving further substances in the process.

DESCRIPTION OF PREFERRED EMBODIMENTS

The above object can be achieved in accordance with the present invention as follows:

The mother liquor which is given by separating terephthalic acid precipitated in the reaction solution through filtration or centrifuge is fed to a heating tube of a relatively small diameter which opens in one end at a separation chamber of a relatively large capacity; the liquor is heated to a temperature above a boiling point of acetic acid under the operation pressure so as to form a mixture mainly composed of solid-gas two phases; the mixture is discharged into the separation chamber to separate solid and gas phases; and the gas phase which mainly comprises acetic acid is drawn out of the separation chamber, and condenses upon being cooled; while the solid phase which comprises the salt(s) the heavy metal, a portion of terephthalic acid and reaction by-products are taken out from the bottom of the separation chamber in the form of discrete powder or easily crushable mass.

The mother liquor may be, prior to feeding into the heating tube, treated in a preliminary evaporation to evaporate a portion of acetic acid in the liquor. The priliminary evaporation can be easily carried out with a conventional thermosiphon reboiler type evaporator. Use of the evaporator is advantageous because share of evaporation in the heating tube and the separation chamber can be reduced, and therefore, necessary capacity of the separation chamber can be also reduced. However, too thickened slurry may cause blocking up of the heating tube, and hence, the preliminary evaporation should be to the extent advantageous for evaporation in the heating tube.

Practical conditions for evaporation in the heating tube are heating temperature, pressure and flow rate, particularly those at the opening end of the tube. They should be chosen in connection with composition of the mother liquor or concentrated mother liquor, diameter of the heating tube, pressure in the separation chamber. Among these factors, the heating temperature and the flow rate are important.

The temperature is of course necessarily above the boiling point of acetic acid under the operation pressure, and preferably, selected from the range at least 20° C. higher than the boiling point. If the temperature difference between the operation temperature and the boiling point is too small to give sufficient super heating, the evaporation in the heating tube is so insufficient that the solid-gas mixture may not be formed in a favorabel form. Thus, it cannot be expected to get the solid component in a powder form or at least a particle ready to be crushed due to imcomplete separation of the volatile component from the solid component. On the other hand, too high the temperature causes adhesion of solid onto inner wall of the heating tube, and accumulation of the solid may finally result in blocking up of the tube. Thus, operation conditions including the heating temperature should be selected experimentalily under a given conditions. Such selection may be easy for those skilled in the art.

As to the pressure inside the separation chamber, though a normal pressure can be employed, a reduced pressure such as 50 to 200 Torr is preferable. In order to obtain a sufficiently high flow rate to form the solid-gas two phase mixture in the heating tube without adehesion of the solid component to inner wall of the tube, it is favorable to realize a vacuum condition in the separation chamber. If the pressure in the separation chamber is low, the pressure in the heating tube may be low, and consequently, the boiling point of acetic acid under the pressure is low. Thus, relatively low temperature of heating can be used. Such a condition is advantageous from view points of easy process control, energy consumption and long life of apparatus. Too large pressure difference between the heating tube and the separation chamber, however, gives a significant temperature decrease due to adiabatic expansion in the separation chamber. The temperature decrease results in, in addition to the originally low operation temperature, undesirably low temperature for a complete separation of volatile components. So, a suitable pressure should be experimentally determined depending of the practical situation.

The present method makes it possible to obtain continuously the solid components in the mother liquor of reaction for terephthalic acid production as a powder or a readily crushable mass, which contains very small amount of acetic acid and water.

Accordingly, recycle and reuse percentage of acetic acid can be increased to the extreme, and it becomes quite easy to recover and reuse the heavy metal components in the solid residue. Solution of troubles in the step of treating the mother liquor ensures stable operation of the main step, the catalytic oxidation, and thus contribute remarkably to the industrial production of terephthalic acid.

EXAMPLE 1

Paraxylene was oxidized with air by using cobalt acetate and manganese acetate as catalyst components and sodium bromide as a promotor, in acetic acid medium. The reaction was regarded as completed when oxygen absorption came to an end, and the reaction mixture was taken out for centrifuge to separate the formed terephthalic acid. The solid substance was washed with acetic acid, and the washing was put together with the filtrate solution.

The mother liquor of reaction thus obtained consisted of: volatile components (acetic acid and water) 76.2% (by weight) and non-volatile components (terephthalic acid, other organic by-products and catalyst components) 23.8%.

The mother liquor was introduced in a heating tube which was heated with steam of 151° C., and discharged in a separation chamber, inside of which was maintained under a pressure of 100 mmHg. The flow rate at the opening end of the heating tube was about 80% of sonic speed. The evaporated components were led to a condensor and liquified, and the solid components were taken out through a valve at the bottom of the separation chamber.

The solid was completely discrete powder, which contained only 0.5% by weight of residual acetic acid. There was observed no blocking up of the heating tube.

EXAMPLE 2

The same mother liquor as was treated in Example 1 was also discharged through a heating tube heated with steam of 151° C. into a separation chamber of 100 mmHg. The flow rate was chosen to be about 14% of sonic speed. No plugging occurred. The product obtained was a mixture of powder and easily crushable masses. Residual acetic acid: 3.5%.

EXAMPLE 3

The same mother liquor as Example 1 was treated in a normal pressure evaporator to remove a portion of acetic acid and water. The obtained slurry contained 51.5% of volatile components and 48.5% of non-volatile components.

The slurry was then introduced in a heating tube which was heated at 180° C. and discharged into a separation chamber of 200 mmHg. The flow rate under these conditions was about 34% of sonic speed. No trouble of plugging was experienced, and the resulting solid component was also discrete powder. Residual acetic acid: 1.1%.

Control Example

The same mother liquor as treated in the above Examples was fed to a heating tube, which was heated with steam of 151° C., and discharged into a separation chamber, inside of which was maintained at 100 mmHg. Feeding of the mother liquor was controled so as to realize a flow rate of about 6% of the sonic speed.

The heating tube soon plugged to become inoperable.

We claim:

1. A method of treating mother liquor of reaction in terephthalic acid production, wherein paraxylene is oxidized with molecular oxygen by using a salt of heavy metal as a catalyst in acetic acid medium, and wherein the terephthalic acid thus formed and precipitated in reaction solution is separated by filtration or centrifuge to give mother liquor of reaction, which method comprising feeding the mother liquor to a tubular type heater having at least one heating tube of a relatively small diameter which opens in one end at a separation chamber of a relatively large capacity, heating the liquor to a temperature above a boiling point of acetic acid under the operating pressure so as to form a mixture mainly composed of solid-gas two phases, discharging the mixture into the separation chamber to separate solid and gas phases, and drawing the gas phase which mainly comprises acetic acid out of the separation chamber and condensing it by cooling, while taking out the solid phase which comprises the salt of the heavy metal, terephthalic acid and reaction by-products from the bottom of the separation chamber in the form of discrete powder or easily crushable mass.

2. A method of claim 1, wherein the mother liquor is fed to the heating tube after being concentrated by evaporating a portion of acetic acid in the liquor.

3. A method of claim 1, wherein the heating in the heating tube is conducted at a temperature at least 20° C. higher than the boiling point of acetic acid under the operation pressure.

4. A method of claim 1, 2 or 3, wherein the treatment is carried out under the condition, at which flow rate of the mixture is at least 1/10, preferably ½ or higher of sonic speed at the opening end of the tube.

5. A method of claim 1, 2 or 3, wherein the treatment is carried out with a pressure in the separation chamber lower than atmospheric pressure.

* * * * *